United States Patent [19]

Stern et al.

[11] Patent Number: 4,942,626
[45] Date of Patent: Jul. 24, 1990

[54] NEEDLESTICK PROTECTIVE GLOVE

[75] Inventors: Joseph A. Stern, Hampton; Stephen L. Green, Newport News; Charles B. King; Sharon B. May, both of Hampton, all of Va.

[73] Assignee: Medev Corporation, Hampton, Va.

[21] Appl. No.: 289,246

[22] Filed: Dec. 23, 1988

[51] Int. Cl.$^5$ ............................................. A41D 19/00
[52] U.S. Cl. ........................................ 2/161 R; 2/163
[58] Field of Search ............... 2/159, 161 R, 163, 167, 2/168, 20, 21

[56] References Cited

U.S. PATENT DOCUMENTS

| | | | |
|---|---|---|---|
| D. 106,139 | 9/1987 | Larom | 2/163 X |
| 133,376 | 11/1872 | Mason | 2/161 R |
| 203,959 | 5/1878 | Townsend | 2/161 R |
| 356,385 | 1/1887 | Waterhouse | 2/20 X |
| 429,653 | 6/1890 | Sholder | 2/16 X |
| 474,929 | 5/1892 | Tabor et al. | 2/163 |
| 709,595 | 9/1902 | Carson | 2/161 R |
| 782,517 | 2/1905 | Niebuhr | 2/21 X |
| 1,083,795 | 1/1914 | Brokaw | 2/159 |
| 1,149,139 | 8/1915 | Heagle | 2/159 |
| 1,351,028 | 8/1920 | Donovan | 2/20 |
| 1,486,006 | 3/1924 | Blom | 2/159 X |
| 1,673,517 | 6/1928 | Kurz | 2/161 R |
| 2,025,710 | 12/1935 | Beemer | 2/159 |
| 2,129,496 | 9/1938 | Hollingsworth | 2/21 |
| 2,309,476 | 1/1943 | Patterson, Jr. | 2/159 |
| 2,443,938 | 6/1948 | Wallis | 2/159 |
| 2,559,788 | 7/1951 | Patternson, Jr. | 2/162 |
| 3,164,841 | 1/1965 | Burtoff | 2/16 X |
| 3,387,306 | 6/1968 | Korey | 2/159 |
| 3,872,515 | 3/1975 | Miner et al. | 2/168 |
| 3,883,898 | 5/1975 | Byrnes, Sr. | 2/167 |
| 4,004,295 | 1/1977 | Byrnes, Sr. | 2/161 R |
| 4,131,952 | 1/1979 | Brenning, Jr. | 2/21 X |
| 4,272,849 | 6/1981 | Thurston et al. | 2/16 |
| 4,384,449 | 5/1983 | Byrnes, Sr. et al. | 2/161 R X |
| 4,416,026 | 11/1983 | Smith | 2/161 R |
| 4,445,232 | 5/1984 | Nelson | 2/161 R |
| 4,470,251 | 9/1984 | Bettcher | 2/161 R X |
| 4,493,865 | 1/1985 | Kuhlmann et al. | 2/16 X |
| 4,507,807 | 4/1985 | Karkanen | 2/21 X |
| 4,573,220 | 3/1986 | Baker | 2/163 X |
| 4,597,108 | 7/1986 | Momose | 2/167 X |
| 4,624,016 | 11/1986 | Luevano | 2/20 X |
| 4,651,514 | 3/1987 | Collett | 2/167 X |
| 4,771,482 | 9/1988 | Shlenker | 2/159 X |
| 4,882,787 | 11/1989 | Hull et al. | 2/163 X |

FOREIGN PATENT DOCUMENTS 0221865  5/1987  European Pat. Off. ............ 2/161 R Primary Examiner—Werner H. Schroeder
Assistant Examiner—Sara M. Current
Attorney, Agent, or Firm—Larson and Taylor

[57] ABSTRACT

A glove for use by medical personnel which is adapted to help prevent accidental injuries when handling needles includes a first discrete layer of flexible material which has a pore size smaller than the diameter of a needle. The first layer forms a glove with at least an opening in the fingerprint area of the index finger stall and middle finger stall. The glove also includes a second discrete layer of flexible material which also has a pore size which is smaller than the diameter of a needle. This second layer is permanently attached to selected areas of the first layer. The selected areas comprise all of the thumb stall, and lateral sides of the index finger stall and middle finger stall.

8 Claims, 1 Drawing Sheet

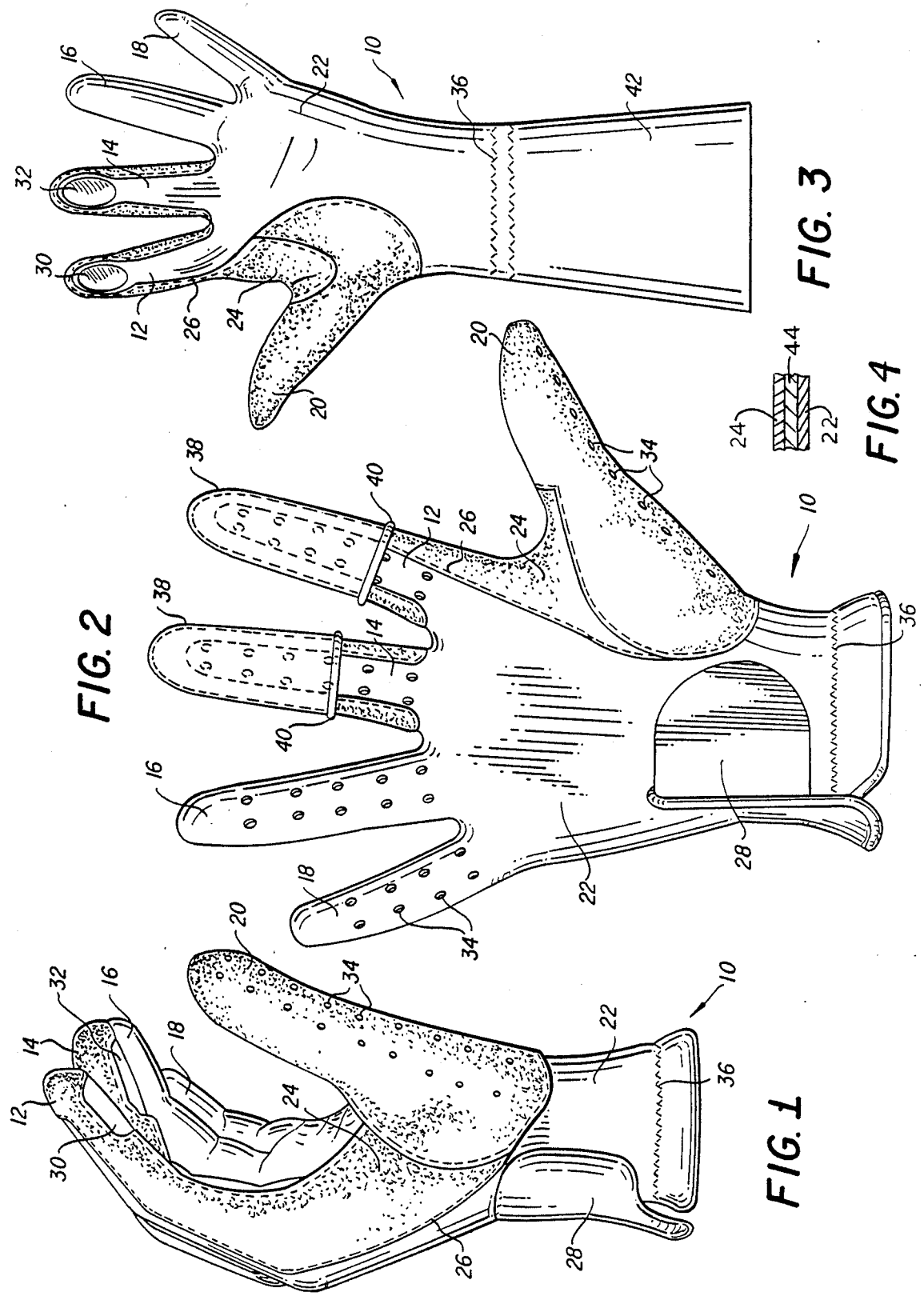

NEEDLESTICK PROTECTIVE GLOVE

BACKGROUND OF THE INVENTION

The present invention relates to a protective glove for medical personnel designed to prevent the wearer from accidently penetrating his or her skin when handling needles. More particularly, the present invention relates to a glove for medical personnel which provides protection from needles and, at the same time, does not significantly interfere with their use of their hands.

Accidents occur when medical personnel are handling needles and particularly when medical personnel attempt to resheath the needle after use. Accidents have occurred whereby the needle enters the sheath at an angle, penetrates the plastic sheath and pricks the user. Also, accidents occur when the needle misses the sheath entirely and sticks the sides of the finger, the thumb or the snuff-box region of the hand.

Needle-handling injuries are particularly dangerous to medical personnel who run the risk of exposure to disease. Highly communicable diseases such as hepatitis-B, and AIDS have caused serious concern to medical personnel treating patients affected by these diseases. Each of these diseases can be communicated to medical personnel as a result of an accidental injury when handling a contaminated needle which has been used to take blood samples or administer intravenous liquids to a patient.

Typically, an intravenous therapy nurse must locate a suitable blood vessel in a patient's limb, normally the arm, by palpating the body part. This requires maximum tactility at the fingerprint area of the index and middle fingers of the nurse in order to locate a suitable blood vessel. Upon location of the blood vessel, the nurse inserts a hypodermic needle through the skin into the vessel to inject a fluid or withdraw the patient's blood which, in either case, contaminates the needle. Once the procedure is complete, the needle is generally resheathed and discarded.

One method for minimizing injuries to medical personnel handling needles is to provide them with protective gloves. A wide variety of protective gloves are known in the art, each of which is designed for its own particular purpose. For example, U.S. Pat. No. 4,416,026 (Smith) issued on Nov. 22, 1983, discloses a multi-purpose mechanic's glove. This glove can be constructed of leather, heat-resistant materials, coated fabrics or combinations of these materials. The glove includes padding to protect the back of the hand, a removable gauntlet which may be joined to the glove with Velcro tape, slide actuated fasteners, straps or buttons, and includes a plurality of holes in the fingertip and palm areas of the glove. The glove provides a workman with hand protection and also allows him to feel the tools or work parts being handled.

U.S. Pat. No. 4,507,807 (Karkanen) issued on Apr. 2, 1985, discloses a work glove finger structure. The glove is constructed from a fabric coated with a suitable material such as neoprene or nitrile butyl rubber. High sensitivity glove tips are attached to a loose-fitting glove by sewing, vulcanizing or gluing. The high-sensitivity tips are made of neoprene or nitrile butyl rubber and are used at the the thumb, index finger and middle finger. A high-friction band of silicone rubber is attached within the finger stall of the glove or molded in the high-sensitivity fingertip covering. The band provides a means for keeping the thin rubber fingertip drawn taut over the fingerprint area to assure improved tactility for the glove wearer.

U.S. Pat. No. 4,624,016 (Luevano) issued on Nov. 25, 1986, discloses an athletic glove with built-in cushioning. A leather glove with a cushion layer and innermost leather layers sewn inside the glove's palm to capture the cushioning material is disclosed. The athletic glove provides impact protection to the wearer's palm.

U.S. Pat. No. 2,309,476 (Patterson, Jr.) issued on Jan. 26, 1943, discloses a glove constructed of leather. The palm side of the glove is formed of two layers of leather cemented together. The inner layer is perforated prior to cementing the outer layer. The cemented layer assembly is then perforated in selected regions for ventilation of the wearer's hand. A partial vacuum results due to the inner layer perforations between the hand and the glove, improving the wearer's grip.

U.S. Pat. No. 3,387,306 (Korey) issued on June 11, 1968, discloses a golf glove constructed of kid's skin, calf skin or kangaroo skin. The glove is assembled of leather by stitching. The glove covers the entire surface of the wearer's hand with the exception of the exposure of the thumb extending from just below the knuckle and exposure of the index finger extending from just below the second knuckle from the fingertip. The glove wearer's sense of touch is improved by the absence of glove coverage of portions of the thumb and index finger. The wearer can use the glove with appropriate golf clubs for both driving and putting without removing the glove.

The foregoing are examples of gloves known in the art which exhibit one or more features which may be useful to medical personnel wearing gloves to prevent accidents when handling needles. However, none of these gloves are satisfactory for use by medical personnel who must palpate to locate a suitable blood vessel and also have sufficient protection for their hands to avoid an accidental needle prick.

Accordingly, there is a need in the art for an improved glove design and method for making such a glove which may be used by medical personnel when handling needles to prevent accidental injuries which might result in exposure to infectious diseases.

SUMMARY OF THE INVENTION

The present invention relates to a glove for use by medical personnel to protect them from accidental injuries when handling needles and which is adapted to cover substantially the entire hand from the wrist to the fingertips. The glove includes a first layer of flexible material having a pore size which is smaller than the diameter of a needle and which forms a glove including four finger stalls and a thumb stall. The first layer also includes at least two openings, one in the fingerprint area of the index finger stall and the second in the fingerprint area of the middle finger stall. The glove further includes a second layer of flexible material having a pore size which is smaller than the diameter of a needle and is attached to selected areas of the first layer of material to provide the selected areas with sufficient thickness to prevent needle penetration under normal conditions encountered when handling needles. In a second aspect, the present invention relates to a method for making a sterile protective glove for use by medical personnel to protect them from accidental injuries when handling needles.

The first step of the method provides a glove-shaped first layer of flexible material having a pore size which is smaller than the diameter of a needle and includes four finger stalls and a thumb stall. Then, a second layer of flexible material having a pore size smaller than the diameter of a needle is attached to selected areas of the first layer of material and the glove is sterilized. The sterilization step may be carried out either by ethylene oxide gas permeation or, in a third aspect of the invention, by immersion in a sporicidal solution.

It is the primary object of the present invention to provide a protective glove for use by medical personnel when handling needles which will prevent an accidental needle prick.

It is a further object of the present invention to provide a protective glove for use by medical personnel when handling needles which does not impair the tactility of the wearer's hand during use.

It is a still further object of the present invention to provide a glove for use by medical personnel when handling needles which is relatively inexpensive and provides satisfactory protection from needle injuries.

It is a still further object of the present invention to provide a glove for use by medical personnel when handling needles which is sterilizable and which may be reused and resterilized.

It is a still further object of the present invention to provide a method for making a sterile protective glove for use by medical personnel when handling needles.

These and other objects of the present invention will be apparent to one of ordinary skill in the art from the detailed description which follows.

BRIEF DESCRIPTION OF THE DRAWINGS

FIG. 1 is a perspective side view of one embodiment of a glove in accordance with the present invention.

FIG. 2 is a perspective view of the back side of a glove in accordance with the present invention, including optional finger cots on the middle and index fingers.

FIG. 3 is a perspective view of the palm side of a glove in accordance with the present invention, including an optional gauntlet.

FIG. 4 is a cross section of a portion of a glove according to the present invention having three layers.

DETAILED DESCRIPTION OF THE PREFERRED EMBODIMENTS

Referring now to FIG. 1, there is shown a side plan view of a protective glove in accordance with the present invention. Glove 10 includes four finger stalls, index or first finger stall 12, middle finger stall 14, third finger stall 16, and pinky finger stall 18. Glove 10 also includes thumb stall 20. Glove 10 is fabricated from a first layer 22 of flexible material and includes a second layer 24 of flexible material attached to selected portions of first layer 22 by any suitable means such as stitching 26. Glove 10 also includes fastening means 28 which is used to open and close the wrist portion of glove 10 to make it easier to take off and put on to the user's hand.

Finally, glove 10 includes two openings therein. The first opening 30 is located in the fingerprint portion of index finger stall 12, and the second opening 32 is located in the fingerprint portion of middle finger stall 14. First and second openings, 30 and 32, are present to improve the tactility of the user's hand when wearing the glove since first and second openings, 30 and 32, allow direct contact between the user's hand and anything that is being touched.

Optionally, glove 10 may also include ventilation openings 34 to allow air to flow into the glove and thereby minimize sweating and discomfort. Further, the preferred glove 10 includes an area of elasticized stitching 36 near the base of the glove in order to provide a snug fit around the user's wrist while at the same time allowing easy entry and exit from the glove.

On FIG. 2 is shown a backside view of glove 10 in accordance with the present invention wherein like elements are designated by like numerals. The embodiment shown in FIG. 2 also includes a pair of finger cots 38 fitted over index finger stall 12 and middle finger stall 14 respectively. Finger cots 38 may be employed when sterility is desirable in order to prevent direct contact between the user's fingertips through first and second openings 30, 32 and the patient. Finger cots 38 may be made of a thin elastomeric material in order to preserve maximum tactility of the glove wearer's fingertips while at the same time preserve sterile conditions. Finger cots 38 preferably include elastic ring 40 which fits tightly about the fingers of the glove wearer in order to maintain finger cots 38 on the fingers as well as to provide a seal between glove 10 and finger cots 38 to thereby prevent contamination from the glove wearer's fingertips from escaping outside finger cots 38. As an alternative to finger cots 38, other gloves such as rubber or latex may be worn over the glove of the present invention to preserve sterility.

Referring now to FIG. 3, there is shown a palm side view of a third embodiment of a glove in accordance with the present invention. Again, like numerals designate like elements. This embodiment of glove 10 includes a gauntlet 42 attached thereto. Gauntlet 42 is an optional modification to glove 10 which improves the gloves ability to be adapted to a sterile environment. Gauntlet 42 may be folded up as a cuff such that glove 10 may be donned in a sterile environment without the user touching any part of the outside of glove 10 and thereby contaminating it.

The protective glove of the present invention is preferably constructed of cabretta leather although other materials such as calfskin, buckskin, kangaroo leather and polyurethane resin impregnated fabric may be employed. The glove is sewn or fabricated of single-ply leather with a second leather ply tailored to fit, cut to size and attached by sewing in selected areas that are deemed vulnerable to needlesticks as shown in FIG. 1. The two-ply construction of the glove is shown along the side of the index and middle finger continuing over the snuff-box region of the hand and fully encompassing the thumb stall. Two-plys of leather have been demonstrated to provide needlestick protection under the normal thrusting forces to resheath a needle. Many needlestick accidents occur when medical personnel attempt to resheath the needle. Accidents have occurred whereby the needle enters the sheath at an angle and penetrates the plastic sheath and pricks the user. Also, accidents have occurred whereby the needle misses the sheath entirely and sticks the sides of the finger, the thumb or the snuff-box region of the hand. The two-ply leather protected areas of the glove of the present invention appear to be the most prevalent areas of needlestick occurrence. However, the glove design could also have areas of reinforcement for all of the fingers and other hand locations if deemed advisable and is not to be considered to be limited to the precise form disclosed in the drawings.

The glove material is soft, supple and allows the wearer to grip, feel and grasp objects. The glove's index and middle fingers each have openings at their extremities to expose the fingerprint areas of the wearer. As a result, the wearer can palpate a patient by direct contact with a patient's skin if desired. If sterility of patient contact is required, sterile rubber or vinyl latex finger cots may be placed over the openings as shown in FIG. 2 with the rolled free edge of the finger cot located between the second and third joint from the tip of the fingers. The finger cots rolled edge allows a compressive force to be applied to the glove's exterior thereby maintaining a taut, drawn latex membrane over the fingerprint region to assure excellent tactility of the wearer.

The leather material is porous to a minimal degree and therefore will absorb liquids and become stained when contaminated with blood. In a preferred embodiment, the glove color is chosen to closely match the color of a dried blood stain to minimize the discoloration of the glove in use. A leather treatment such as a silicone finish may impart anti-wetting properties to the surface of the leather. Such a finish would prevent bloodstain discoloration and still maintain the porosity of the leather permitting it to breathe.

An important feature of the glove of the present invention is that it is sterilizable and useful under sterile conditions. Three different sterilization procedures have been successfully applied to the glove of the present invention. The first, and most preferred procedure, utilized ethylene oxide gas at 130° F. The glove is permeated by ethylene oxide gas for a period of 1¾ hours up to a 4-hour maximum dwell time, followed by a 12-hour room-temperature aeration. This sterilization process appeared to have a minimal effect on the coloration, size and flexibility of the glove leather. This procedure, although expensive, is a satisfactory approach to glove sterilization.

A second sterilization procedure was also found to be satisfactory, although less preferred than the ethylene oxide procedure. This procedure involves immersion of a leather glove in a sporicidal solution such as (a solution of 0.13% glutarldehyde-phenate complex, alkaline solution diluted 1 part solution to 16 parts sterile water). This procedure had a minimal effect on the color of the leather, the size of the glove finger and the feel of the leather. The 10 to 15 minute time of glove immersion in the glutarldehyde solution followed by a thorough rinsing and drying will sterilize the glove. A glove test sample was immersed for 24 hours followed by rinsing and drying, and this sterilization cycle is equivalent to approximately 100 glove immersions at 10–15 minutes per cleaning cycle, thus indicating that the glove could be sterilized by repeated immersion and drying cycles and still maintain its serviceability. However, this procedure is less preferred since residual Sporicidin solution must be thoroughly removed from the glove to prevent skin irritation to the wearer of the glove.

A third sterilization procedure was developed to disinfect the outer surface of the glove while being worn by a medical specialist. A hexachlorophene foam disinfectant such as septisol foam can be applied by the glove wearer using the manufacturer's instructions for disinfecting the skin. This procedure permits glove contact area sterilization for use in field emergencies and for multi-patient care without the time delay required by ethylene oxide gas or sporicidal solution immersion sterilization procedures.

In use, the glove is developed specifically for an intravenous therapy nurse. Generally, the nurse must locate a suitable blood vessel in the patient's limb, normally the arm, by palpating the patient which requires maximum tactility at the fingerprint area of the index and middle fingers. Upon location of a suitable blood vessel, the nurse inserts a hypodermic needle through the skin and into the subject vessel to inject a fluid or withdraw the patient's blood which, in either case, contaminates the needle. The glove of the present invention prevents the wearer from accidentally penetrating his or her skin when handling such contaminated needles and, thus, minimizing exposure to highly-communicable diseases such as hepatitis B, and AIDS.

The glove could also be utilized by hematologists and laboratory technicians, where glasswear containing blood samples is processed. Accidents have occurred whereby glasswear fractured in the technician's hand and glass chards contaminated with diseased blood penetrated the technician's skin. The glove of the present invention provides some limited protection from glass chard penetration.

In a sterile environment, the glove design of the present invention can be modified with a gauntlet 42 as shown in FIG. 3 in order to permit the wearer to don the glove in the sterile environment. The gauntlet would be folded upwardly when the glove is sterilized and packaged to form a cuff and the user would handle only the cuff when donning the glove. Once the glove is on, the cuff would be pulled down to form the gauntlet and the outside of the glove would remain uncontaminated. The glove may be worn on either hand or both hands if desired to provide limited cut protection, glass chard penetration resistance and needlestick protection.

Another method of needlestick protection in accordance with the present invention would utilize needle impenetrable insert layer 44 placed as shown in FIG. 4 between the first and second layers of leather in the area to be reinforced. This reinforcement ply would be chosen for its needlestick protection and also for its ability to flex, allowing the fingers of the wearer a minimum restraint in performance of their normal functions. Suitable needle impenetrable insert layers would be materials having very small pore sizes which would not allow penetration of a needle without significant forces being exerted.

The following examples are provided to illustrate the fabrication of a needlestick protective glove in accordance with the present invention.

EXAMPLE 1

Seven identical gloves of white cabretta leather were purchased. Six of these gloves were sterilized using ethylene oxide gas, using the sterilization facilities of a local hospital. The glove tests were conducted with guidelines for each of the gloves to be sterilized a different number of cycles ranging from 1 cycle to 24 cycles. One glove, identical to the 6 sterilized gloves, was used as a control sample and did not undergo sterilization, thus permitting comparison of fit, color, feel and appearance to determine if the sterilization procedure degraded these properties. Each sterilization cycle involved exposure to ethylene oxide gas at a temperature of 130° F., for one and three-fourths to a maximum of four hours followed by an aeration cycle of twelve hours in a circulating air environment.

Glove 1 was subjected to one ethylene oxide sterilization cycle. The glove leather appeared soft, supple and without any noticeable color change. The fit of the glove appeared slightly more snug than the control sample as a result of the sterilization processing. The sheen of the glove appears to have been lost after the one cycle as compared with the control sample glove.

Glove 2 was subjected to four ethylene oxide sterilization cycles. The glove leather appeared soft and supple with a minimum of discoloration. The glove shrank as evidenced by the amount of Velcro flap overlap and by the feel of the glove's fit on the hand.

Glove 3 was subjected to eight ethylene oxide sterilization cycles. The glove leather remained soft and supple with minimal color change. The glove shrank in size as indicated by the Velcro flap overlap and the glove's fit appeared more snug, but was entirely satisfactory.

Glove 4 was subjected to twelve ethylene oxide sterilization cycles. The leather appeared soft and supple, some glove shrinkage had occurred but the glove had a satisfactory fit. The Velcro flap did not overlap as far as the control glove, indicating some leather shrinkage had occurred.

Glove 5 underwent 18 ethylene oxide sterilization cycles. The leather still appeared soft and supple. The ring and little finger of the glove had one spot each on the palm side where the leather appeared stiffer. These two spots may have been contaminated during the glove making procedure or packaging operations. The leather color appeared slightly less white than the control sample. The glove had shrunk in size as indicated by the Velcro flap overlap and felt snug on the hand when compared with the control sample glove. The fit of the glove was still entirely satisfactory.

Glove 6 underwent 24 ethylene oxide sterilization cycles. The color of the leather had only slightly yellowed as compared with the control sample and the leather had remained soft and supple. The glove had shrunk as indicated by the amount of Velcro flap overlap and the fit of the glove compared with the control sample. However, the fit was still entirely satisfactory.

The ethylene oxide sterilization cycle appeared to have a slight effect upon the leather of the glove with increasing shrinkage as related to the number of sterilization cycles. All of the gloves remained substantially white and the fit was entirely adequate. It is anticipated that the gloves will stretch slightly with wear and these gloves were not worn at any time other than the initial trial fit prior to sterilization. Therefore, they were not subjected to hand oils and perspiration as would be expected in normal usage.

The foregoing description of embodiments of the invention has been presented for purposes of illustration and description only. Many modifications and variations will be apparent to one of ordinary skill in the art in light of the above teachings. Accordingly, the scope of the invention is to be defined by the claims appended hereto.

What is claimed is:

1. A glove for use by medical personnel to protect them from accidental injuries when handling needles which is adapted to cover substantially the entire hand from the wrist to the fingertips which comprises:
    a first discrete layer of a flexible material having a pore size which is smaller than the diameter of a needle and which forms a glove including four finger stalls and a thumb stall, said first layer including at least two openings, one in the fingerprint area of the index finger stall and the second in the fingerprint area of the middle finger stall, and
    a second discrete layer of flexible material having a pore size which is smaller than the diameter of a needle, said second layer being permanently attached to selected areas of said first layer of material to provide said selected areas with sufficient thickness to prevent needle penetration under normal conditions encountered when handling needles, said selected areas comprising all of said thumb stall, and lateral sides of said index finger stall and said middle finger stall.

2. A glove as claimed in claim 1 wherein said selected areas further comprise an extension of said second layer of said thumb stall and adjacent lateral side of said index finger stall to the snuff box region of the glove.

3. A glove as claimed in claim 1 further comprising at least two finger cots worn over said index and middle finger stalls.

4. A glove as claimed in claim 1 further comprising a plurality of ventilation perforations on the back side of the glove.

5. A glove as claimed in claim 4 which is sterilized.

6. A glove as claimed in claim 5 wherein the glove has been sterilized by treatment with ethylene oxide gas.

7. A glove as claimed in claim 5 further comprising a gauntlet to permit the wearer to don the glove in the sterile environment.

8. A glove as claimed in claim 1 wherein said selected areas comprise the entire second layer of the glove and the glove further comprises a third, substantially needle impenetrable layer located in said selected areas between said first and said second layers.

* * * * *